(12) United States Patent
Pralong et al.

(10) Patent No.: US 8,845,902 B2
(45) Date of Patent: Sep. 30, 2014

(54) PNEUMATIC ALTERNATING PRESSURE MEMBRANE CELL SEPARATION SYSTEM

(75) Inventors: Alain Pralong, Grand-Leez (BE); Hans Ulrich Dellenbach, Thörishaus (CH)

(73) Assignee: Crucell Holland B.V., Leiden (NL)

( * ) Notice: Subject to any disclaimer, the term of this patent is extended or adjusted under 35 U.S.C. 154(b) by 0 days.

(21) Appl. No.: 13/983,982

(22) PCT Filed: Feb. 7, 2012

(86) PCT No.: PCT/EP2012/052031
§ 371 (c)(1),
(2), (4) Date: Aug. 6, 2013

(87) PCT Pub. No.: WO2012/107436
PCT Pub. Date: Aug. 16, 2012

(65) Prior Publication Data
US 2013/0319944 A1    Dec. 5, 2013

Related U.S. Application Data

(60) Provisional application No. 61/463,095, filed on Feb. 10, 2011, provisional application No. 61/627,812, filed on Oct. 18, 2011.

(30) Foreign Application Priority Data

Feb. 10, 2011  (EP) .................................... 11153995
Oct. 3, 2011   (EP) .................................... 11183676

(51) Int. Cl.
| | | |
|---|---|---|
| *B01D 61/00* | (2006.01) | |
| *B01D 63/00* | (2006.01) | |
| *B01D 35/00* | (2006.01) | |
| *B01D 21/24* | (2006.01) | |
| *B01D 63/02* | (2006.01) | |
| *B01D 65/02* | (2006.01) | |
| *B01D 61/22* | (2006.01) | |
| *B01D 61/20* | (2006.01) | |

(52) U.S. Cl.
CPC ................ *B01D 63/02* (2013.01); *B01D 65/02* (2013.01); *B01D 2321/04* (2013.01); *B01D 61/22* (2013.01); *B01D 2313/243* (2013.01); *B01D 61/20* (2013.01)
USPC ............... 210/650; 210/85; 210/86; 210/100; 210/321.8; 210/257.2; 210/416.1

(58) Field of Classification Search
CPC .................. C02F 2201/46115; C02F 2209/03; C02F 2201/4612; B01D 61/54; B01D 29/663; B01D 2321/2083; B01D 61/46; B01D 63/02
USPC .................. 210/257.2, 767, 650, 636, 195.2, 210/321.69, 416, 1, 85, 86, 100, 321.8, 210/321.75; 435/243
See application file for complete search history.

(56) References Cited

U.S. PATENT DOCUMENTS

| | | | | |
|---|---|---|---|---|
| 4,502,953 | A | * | 3/1985 | Marsh et al. .................... 210/94 |
| 4,861,498 | A | | 8/1989 | Robinsky et al. |
| 5,039,402 | A | * | 8/1991 | Himelstein ..................... 210/121 |
| 5,234,424 | A | * | 8/1993 | Yum et al. ................... 604/892.1 |
| 5,254,243 | A | * | 10/1993 | Carr et al. ......................... 210/94 |
| 5,256,279 | A | * | 10/1993 | Voznick et al. ................. 210/86 |
| 5,324,424 | A | * | 6/1994 | Hochgatterer ................ 210/123 |
| 5,911,884 | A | * | 6/1999 | Boulter ......................... 210/739 |
| 6,093,312 | A | * | 7/2000 | Boulter ........................... 210/86 |
| 6,544,424 | B1 | | 4/2003 | Shevitz |
| 7,288,195 | B2 | * | 10/2007 | Coville et al. ............ 210/321.75 |
| 2004/0104152 | A1 | | 6/2004 | Mukai |
| 2004/0217053 | A1 | | 11/2004 | Zha et al. |
| 2009/0223895 | A1 | | 9/2009 | Zha et al. |
| 2010/0078395 | A1 | | 4/2010 | Shevitz |
| 2013/0270165 | A1 | * | 10/2013 | Shevitz ......................... 210/151 |

FOREIGN PATENT DOCUMENTS

| | | |
|---|---|---|
| DE | 202005018578 U1 | 5/2007 |
| EP | 0322753 A2 | 12/1988 |
| EP | 1424119 A2 | 6/2004 |
| WO | 03013706 A1 | 2/2003 |
| WO | 2008006494 A1 | 1/2008 |

| WO | 2010036338 A1 | 4/2010 |
| WO | 2010060719 A1 | 6/2010 |
| WO | 2012107436 A1 | 8/2012 |

OTHER PUBLICATIONS

PCT International Preliminary Report on Patentability, PCT/EP2012/052031 dated Aug. 29, 2013.

PCT International Search Report, PCT/EP2012/052031 dated Apr. 18, 2012.

\* cited by examiner

*Primary Examiner* — Ana Fortuna (74) *Attorney, Agent, or Firm* — TraskBritt, P.C.

(57) ABSTRACT

Provided are filtration systems that can be referred to as Pneumatic Alternating Cell Separator (PACS), useful components thereof in the form of assemblies or kits of parts that can be used to build the system, and use of the system for filtering fluids, for instance, in cell culture perfusion systems comprising a filter-containing chamber, an expansion chamber and a gas flow controller.

17 Claims, 4 Drawing Sheets

PNEUMATIC ALTERNATING PRESSURE MEMBRANE CELL SEPARATION SYSTEM

CROSS-REFERENCE TO RELATED APPLICATIONS

This application is a national phase entry under 35 U.S.C. §371 of International Patent Application PCT/EP2012/052031, filed Feb. 7, 2012, designating the United States of America and published in English as International Patent Publication WO 2012/107436 A1 on Aug. 16, 2012, which claims the benefit under Article 8 of the Patent Cooperation Treaty and under 35 U.S.C. §119(e) to U.S. Provisional Patent Application Ser. No. 61/627,812, filed Oct. 18, 2011, to European Patent Application Serial No. 11183676.3, filed Oct. 3, 2011, to U.S. Provisional Patent Application Ser. No. 61/463,095, filed Feb. 10, 2011, and to European Patent Application Serial No. 11153995.3, filed Feb. 10, 2011.

TECHNICAL FIELD

The disclosure relates to filtration systems. More specifically, the invention relates to a Pneumatic Alternating Cell Separation (PACS) system for fluids, particularly biological fluids comprising cells.

BACKGROUND

Filtration is typically performed to separate, clarify, modify and/or concentrate a fluid solution, mixture or suspension. In the biotechnology and pharmaceutical industries, filtration is vital for the successful production, processing, and testing of new drugs, diagnostics and other biological products. For example, in the process of manufacturing biologicals, using animal cell culture, filtration is done for clarification, selective removal and concentration of certain constituents from the culture media or to modify the media prior to further processing. Filtration may also be used to enhance productivity by maintaining a culture in perfusion at high cell concentration. The invention provides an improved means for fractionating a mixture or suspension of molecules or particulates based on physical and/or chemical properties.

Several specialized filters and filtration methods have been developed to separate materials according to their chemical and physical properties. Filters that have been developed in the art include flat surface filters, pleated filters, multi-unit cassettes, and tubular forms such as hollow fibers. However, many of these filters have short operating lives, and when used to filter cell culture suspension or other biological fluids, they tend to clog with dead cells, cell debris, aggregates or other constituents of the fluid.

Animal cells grow substantially slower than most microorganisms, and lacking protective cell wall, they are also more fragile. Some known methods for increasing the productivity of microbial culture production, including increasing agitation rates and vigorous delivery of gases into the culture, are not feasible with animal cells. Thus, production is limited to very gentle culture conditions and low cell concentrations. One way to increase the cell concentration while maintaining gentle culture conditions is through the perfusion method.

In the perfusion method for growing cells, culture medium, whose nutrients have been consumed and which contains increased levels of harmful waste products, is continuously removed from the culture and replaced with fresh medium. The constant addition of fresh medium while eliminating waste products provides the cells with the nutrients required to achieve high cell concentrations. Unlike the constant changing conditions during the batch culture method of production, the perfusion method offers the means to achieve and maintain a culture in steady state.

In normal batch culture production processes, cells are first inoculated into a fresh medium and the cells rapidly enter a log grow phase. As they consume the medium nutrients and waste products accumulate, the cells transition to a stationary phase followed by a decay phase. While several methods have been developed to optimize batch culture production, in each case, these processes undergo rapid growth and decay cycles. In perfusion, however, since waste products generated by the culture are continuously removed and the culture is continuously replenished with fresh medium, it is possible to achieve a state of equilibrium in which cell concentration and productivity are maintained. Typically, about one culture volume is exchanged per day and the cell concentration achieved in perfusion are typically two to more than ten times that achieved at the peak of batch culture.

Filtration systems for biological fluids were described previously in the art. One type of external filtration perfusion system is, for instance, described in U.S. Pat. No. 6,544,424, which is incorporated herein by reference. This fluid filtration system comprises a fluid storage vessel connected to a filter-containing compartment that is connected to a diaphragm pump. The diaphragm pump alternatively aspirates the fluid out of the vessel through the filter and expels the fluid through the retentate end of the filter, back into the vessel. By doing so, the system creates an alternating tangential flow of fluid through the filter element.

A major drawback of this system is that the diaphragm pump contains moving parts that are prone to wastage and can often break during the process. When the diaphragm breaks, the filtration system is no longer closed and becomes susceptible for contamination. The filtration process must, therefore, be aborted, leading to high costs in the case of e.g., processes for production of biopharmaceuticals. Indeed, since processes for the production of biopharmaceutical molecules take several days, sometimes up to several weeks, the breakage of a pump during a process run would lead to high costs and long down time in a production facility. It takes up to days for getting a new process running. These perfusion cultures are mainly performed at the last stage of the production process, which means that a lot of time and money is wasted due to this failure. It usually takes three to five weeks before the stage of perfusion is reached. The costs involved can easily increase to more than over $100,000.

A second drawback is that the diaphragm pump described in U.S. Pat. No. 6,544,424 consists of a stainless steel jacket that contains a diaphragm usually made of rubber or silicone. Before each run, the elements of the diaphragm pump must be cleaned, assembled and sterilized. In addition, when the system is used for production of pharmaceutical products, the cleaning and sterilization procedures must be validated. That validation requires lengthy procedures and test runs, which are very costly and time consuming.

A third drawback of the systems currently in use is that they use invasive sensor technology where sensors are in contact with the product and those sensors cannot be replaced during the process.

The disclosure aims at providing improved fluid filtration systems that have less of, or even eliminate, these drawbacks.

DISCLOSURE

Provided is a novel filtration system that can be referred to as Pneumatic Alternating Cell Separator (PACS), useful components thereof in the form of assemblies or kits of parts that can be used to build the system, and use of the system for filtering fluids, for instance, in cell culture perfusion systems. Provided is a filtration system comprising a vessel connected to an entrance end of a filter-containing compartment that, at the exit end, is connected to an expansion chamber, which is connected to a gas flow controller. The gas flow controller alternately provides for positive and negative pressure into the expansion chamber, allowing for the fluid contained in the storage vessel to be alternately aspirated through the filter element into the expansion chamber and expelled from the expansion chamber, through the filter, and back into the vessel. By doing so, the system creates an alternating tangential flow of fluid through the filter element. The fluid flow can further be guided through a fluid harvest port into a recovery container. The system is useful for conducting a rapid, low shear, tangential flow filtration. Such a system has applications in perfusion of cultured animal cells, as well as other varied filtration applications.

The system hereof offers the benefits of tangential flow filtration without some of its drawbacks. As will become apparent, some of the benefits not offered by other systems in the art include the absence of moving parts, which are required in similar systems to provide for the alternating liquid flow. Indeed, certain systems known in the art comprise a diaphragm pump that alternately aspirates the fluid out of the vessel through the filter-containing compartment and expels the fluid through the retentate end of the filter, and back into the vessel. The diaphragm, which is a fragile rubber membrane, can easily rupture when extensively used.

The system does not require a diaphragm pump that can easily break, nor any moving parts that are prone to wastage due to extensive use of the system. The system comprises an expansion chamber, with at least two openings, which is connected on one side (first opening) to the exit end of a filter-containing compartment allowing for liquid from that compartment to enter the chamber and on the other side (second opening) to a gas flow controller, which alternately provides negative and positive pressure into the expansion chamber, thereby aspirating fluid from the exit end of the filter-containing compartment and expelling fluid back into the exit end of the filter-containing compartment.

Herewith, the expansion chamber in the present system comprises a direct gas-liquid interface without separation means, the interface being formed by the liquid contained in the system that is in direct contact with the gas phase provided by the gas flow controller. The expansion chamber does not contain any separation means between the first and second opening of the chamber. The expansion chamber comprises one room or space and is not separated into two or more compartments. The absence of separation means, such as a diaphragm, or any other moving parts, increases the lifetime of the system and minimizes the risks of premature abortion of a process cycle.

In addition, the filtration system, according to preferred embodiments, does not require costly cleaning and sterilization validation. Instead, it comprises in such embodiments disposable elements that are pre-sterilized and ready for use. This offers a great advantage considering validation costs and assembly time.

In further preferred embodiments, a third remarkable advantage of the system is that it uses noninvasive sensors. The filtration system hereof uses sensors that are not in contact with product and that can be replaced in-process when broken. This allows for a more controlled process environment during the whole length of the process run.

Provided is a fluid filtration system comprising:
a) at least one fluid storage vessel;
b) at least one filter-containing compartment;
c) at least one fluid transfer line connecting the storage vessel to an entrance end of a filter-containing compartment, which fluid transfer line is capable of directing a fluid from the storage vessel into the entrance end of the filter-containing compartment;
d) at least one expansion chamber with at least two openings,
wherein a first opening is connected at an exit end of the filter-containing compartment and wherein a second opening is connected to a gas flow controller, and wherein the expansion chamber contains no separation means between the first and second opening;
e) at least one gas flow controller for alternately providing the expansion chamber with positive and negative pressure;
f) at least one fluid harvest port connected to the filter-containing compartment for removing filtered fluid from the filter-containing compartment.

In one embodiment, the expansion chamber is connected to the gas flow controller with a gas line. In one embodiment, the gas line comprises a sterile filter between the expansion chamber and the gas flow controller. In one embodiment, the sterile filter is provided with a heater.

In one embodiment, the fluid storage vessel is a bioreactor.

In one embodiment, the filter-containing compartment contains a hollow fiber filter. In another embodiment, the filter-containing compartment contains a screen filter.

In yet another embodiment, the fluid filtration system according to the invention comprises at least one level sensor mounted on the surface of the expansion chamber.

In a preferred embodiment, the fluid filtration system comprises at least one level sensor mounted on or in the expansion chamber, preferably wherein at least two level sensors are mounted on or in the expansion chamber, and preferably wherein the level sensor is (or level sensors are) mounted on the surface (i.e., outside) of the expansion chamber.

In one embodiment, the level sensors are capable of measuring minimal and maximal fluid levels in the expansion chamber, and are functionally coupled to the gas flow controller.

In one embodiment, the fluid filtration system according to the invention is capable of alternately aspirating the fluid of the system from the storage vessel, through the filter-containing compartment into the expansion chamber, and expelling the fluid from the expansion chamber through the filter-containing compartment back into the storage vessel. Fluid aspiration is performed by applying negative pressure into the expansion chamber and fluid expulsion is performed by applying positive pressure into the expansion chamber.

Preferably, the negative pressure is obtained by creating a vacuum in the expansion chamber and positive pressure is obtained by injecting gas, for instance, compressed air, into the expansion chamber.

In one preferred embodiment, the fluid filtration system comprises:
a) at least one fluid storage vessel;
b) at least one filter-containing compartment; wherein the filter comprises a plurality of bundled hollow fibers whose axes extend longitudinally from the entrance end to the exit end of the filter-containing compartment;
c) a fluid transfer line connected at one end thereof to the storage vessel, and attached at another end thereof to an entrance end of the filter-containing compartment, which fluid transfer line is capable of directing a fluid from the storage vessel into the entrance end of the filter-containing compartment;

d) at least one expansion chamber connected at a retentate exit end of the filter-containing compartment; which expansion chamber is capable of alternately aspirating fluid from the retentate exit end of the filter-containing compartment and expelling the fluid back into the retentate exit end of the filter-containing compartment, the expansion chamber being connected to a gas flow controller capable of alternately applying negative and positive pressure into the expansion chamber and thereby forming a direct gas-liquid interface without separation means into the expansion chamber; and e) at least one fluid harvest port connected to the filter-containing compartment for removing filtered fluid from the permeate exit end of the filter-containing compartment, the harvest port optionally being connected via a permeate line to a fluid pump.

In certain embodiments, the filter-containing compartment and/or the expansion chamber are disposable, i.e., made of disposable materials, and in further preferred embodiments, the fluid storage vessel and/or the fluid transfer line are also disposable. Preferably, the complete fluid filtration system is disposable.

Another aspect hereof relates to an assembly comprising an expansion chamber assembled to a filter-containing compartment on one side and to an air filter on the other side. Preferably, the assembly is capable of being functionally coupled to a gas line that can provide positive and negative pressure to the expansion chamber. Preferably, the assembled components exclusively comprise disposable materials.

Another aspect hereof relates to a kit of parts comprising an expansion chamber, a filter-containing compartment and an air filter, intended for providing an assembly as described herein.

Also provided is a process for filtering a fluid comprising the steps of:

a) providing a fluid filtration system comprising:
   at least one fluid storage vessel;
   at least one filter-containing compartment;
   a fluid transfer line connecting the storage vessel to an entrance end of the filter-containing compartment, which transfer line is capable of directing a fluid from the storage vessel into the entrance end of the filter-containing compartment;
   at least one expansion chamber connected on one side to an exit end of the filter-containing compartment allowing for liquid from that compartment to enter the chamber and on the other side to a gas flow controller that alternately provides negative and positive pressure into the expansion chamber, thereby aspirating fluid from the exit end of the filter-containing compartment and expelling fluid back into the exit end of the filter-containing compartment, forming a direct gas-liquid interface without separation means into the expansion chamber; and
   at least one permeate port connected to the filter-containing compartment for removing filtered fluid from the filter-containing compartment;

b) filtering a fluid by causing the fluid to flow from the storage vessel through the filter-containing compartment into the expansion chamber by applying negative pressure into the expansion chamber;

c) re-filtering the fluid by causing at least a portion of the fluid to flow from the expansion chamber through the filter back into the storage vessel by applying positive pressure into the expansion chamber;

d) optionally repeating steps b and c; and e) removing the filtered fluid from the filtration system.

Also provided is a process for filtering a fluid hereof, wherein the process is performed using a fluid filtration system hereof.

In a preferred embodiment of the process, the filter-containing compartment and/or the expansion chamber are disposable. Preferably, the filter-containing compartment, the expansion chamber, the fluid storage vessel and the fluid transfer line are disposable.

In another embodiment, the positive and negative pressure are regulated during the process by level sensors that measure the fluid level in the expansion chamber. The level sensors are preferably mounted on the expansion chamber.

DETAILED DESCRIPTION

The disclosure concerns a fluid filtration system generally comprising at least one fluid storage vessel, a fluid transfer line for directing fluid from the vessel through a filter-containing compartment, at least one expansion chamber connected to the filter-containing compartment on one side by means of a fluid connector and to a gas flow controller on the other side by means of a gas line, and at least one fluid harvest port coming out of the filter-containing compartment. The gas flow controller alternately provides for vacuum or compressed air into the expansion chamber in order to power the fluid in alternating directions through the filter-containing compartment. Herewith, a direct gas-liquid interface is formed in the expansion chamber between the fluid in the system and the compressed air provided by the gas flow controller. A separation means between the liquid and gas phase is not required in the present system, contrary to systems known in the art, which, for example, comprise a diaphragm pump that expels and aspirates the fluid in and out of the filter-containing compartment. The absence of a diaphragm pump or other moving parts in the disclosure increases the lifetime of the system and minimizes the risks of premature abortion of a process cycle, as a diaphragm pump or other moving parts can easily break.

The system offers a gentle treatment of fragile materials such as animal cells and biomolecules. A uniform flow can be generated across the entire filter, herewith providing a means for generating rapid, low shear, tangential flow. The system has applications in perfusion of cultured animal cells, as well as other varied filtration applications. Hollow fiber (HF) type filters afford longer operating lives, and they are available in many sizes, configurations, materials, pore sizes and porosity. Furthermore, the process need not be limited to the use of hollow fiber filters. It is possible to insert other separation devices in the hollow fiber housing. One such device is a screen module consisting of a screen mesh as the separation matrix. All such separation modules will be referred to, collectively, as the "filter element" or simply as the "filter."

Figure 1:
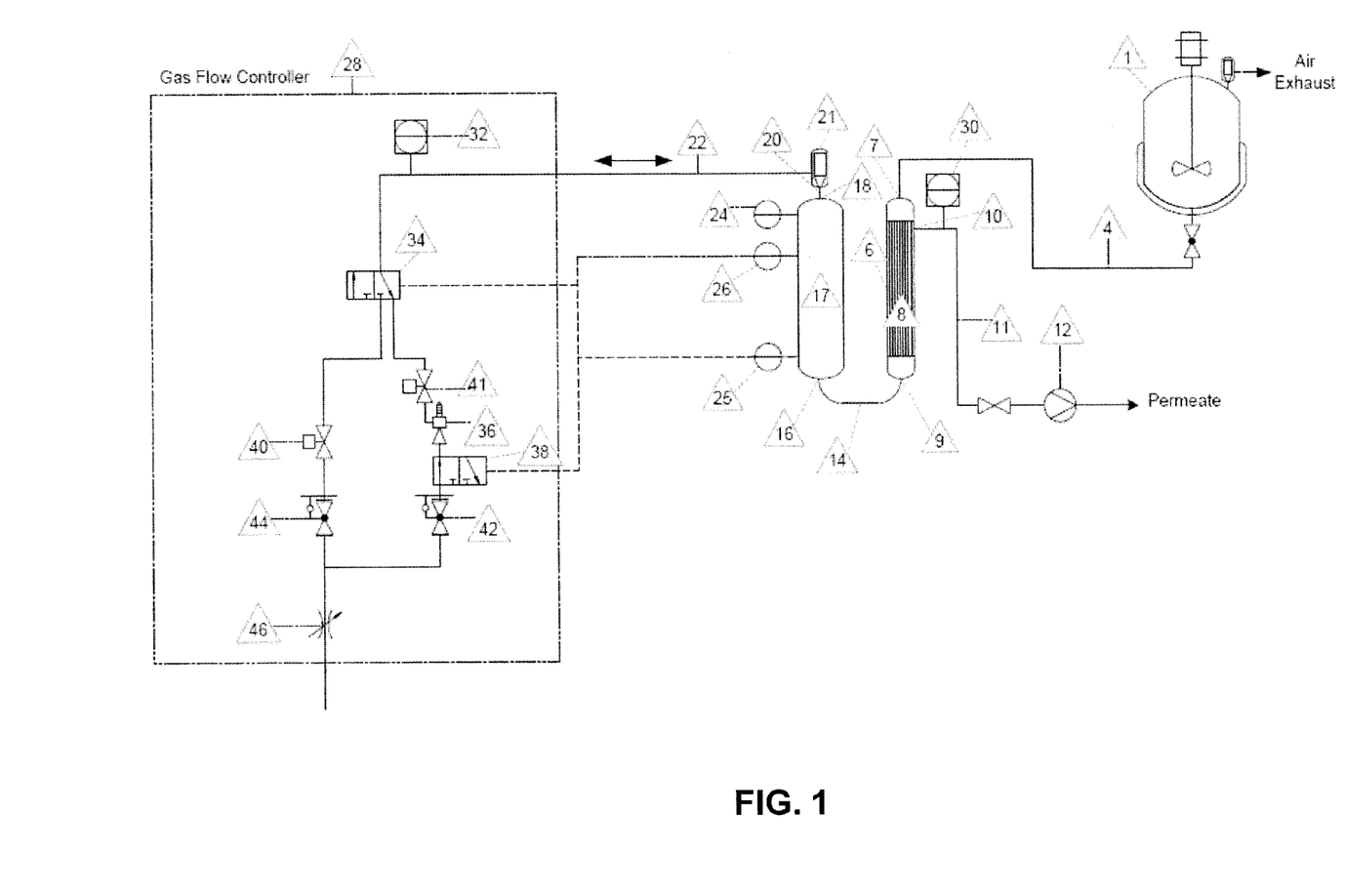
FIG. 1 shows a first embodiment of an alternating tangential flow filtration system according to the invention showing a harvest port at the bottom side of the vessel connected to the bottom side part of a filter compartment.

Referring to FIG. 1, there is shown a fluid filtration system according to the invention. A process vessel or liquid storage vessel (1) is connected via a fluid transfer line (4) to a filter-containing compartment (6). The vessel (1) may be any suitable container for a fluid to be filtered. For example, it may be a bioreactor, a fermentor or any other vessel, nonexclusively including vats, barrels, tanks, bottles, flasks, containers, and the like that can contain liquids. The vessel may be composed of any suitable material such as Ultra Low Density Poly Ethylene (ULDPE), Low Density Polyethylene (LDPE), multilayer materials like the CX5-14 film, polyester, tie barrier layer, Ethyl Vinyl Alcohol (EVOH), and a Polyester Elastomer (PE), or a multilayer material that contains PET, PA, EVOH and ULDPE, metal such as stainless steel, glass, or the like.

The fluid transfer line (4), also referred to as connector or fluid connector, serves to direct a fluid (which is to be filtered and thus may contain particulate material, e.g., cells, but for brevity will be referred to as "fluid" herein) from the storage vessel (1) into an entrance end (7) of the filter-containing compartment (6). The fluid transfer line (4) may comprise a vessel port, suitable for flowing fluid into and out of the vessel (1), attached to a joint, which, in turn, is connected to the entrance end (7) of the filter-containing compartment (6). Suitable ports nonexclusively include any sanitary, leak-proof fittings known in the art such as a compression, standard Ingold or a sanitary-type fitting. Suitable joints nonexclusively include pipes, tubes, hoses, hollow joint assemblies, and the like. The joint may vary from one system to another, based on the configuration and requirements of the vessel and process. In a preferred embodiment, the fluid transfer line (4) is connected to the entrance end (7) of the filter-containing compartment (6) via a tube connection, such as silicone rubber, C-flex, bioprene or dry-to-dry aseptic connections as, e.g., READYMATE® connections from GE Healthcare, or Kleenpack sterile connectors from Pall. The fluid transfer line (4) may also be connected to the vessel (1) and the filter-containing compartment (6) by means of valves and suitable clamps, such as a triclamp sanitary fitting or the like. This does not preclude the use of other appropriate connections.

In one embodiment, the fluid filtration system comprises a tubing as the fluid transfer line, connected between the fluid storage vessel (1) and the filter-containing compartment (6).

In one embodiment, the fluid transfer line (4) is connected at one end thereof to the storage vessel by a valve, and attached at another end thereof to an entrance end (7) of the filter-containing compartment (6) by a valve.

The filter-containing compartment (6) preferably has an entrance end (7) and an exit end or retentate end (9). The name "retentate end" means that the fluid (with possible particulate material) that is being filtered and remains within the lumen of the filter, i.e., does not pass the pores of the filter to the other side of the membrane, which fluid is called the retentate, can pass this end. Material that passes through the pores of the filter is called the "permeate" or also the "filtrate" and, therefore, another possible exit end of the filter compartment, referred to as permeate port (10) or fluid harvest port can be provided to the filter-containing compartment, which permeate port allows the tangential fluid flow to be recovered or harvested. In certain embodiments, the fluid filtration system further comprises at least one permeate pump (12) or filtrate pump connected to the permeate port (10). The entrance end (7) of the filter-containing compartment is connected to the fluid transfer line (4). The retentate exit end (9) of the filter-containing compartment (6) is connected to an expansion chamber (17). The filter-containing compartment (6) can be connected to the expansion chamber (17) directly by an appropriate connection or, for instance, through the intermediate of a fluid transfer line (14) (as shown in FIG. 1). In one embodiment, the exit end (9) is connected directly to the expansion chamber (17) by means of a dry-to-dry aseptic connection, e.g., READYMATE® connections from GE Healthcare, and a clamp (not shown). In another embodiment, the exit end (9) is connected to the expansion chamber (17) by means of a fluid transfer line (14). Preferably, the fluid transfer line (14) is in the form of a tube assembly but other types of connectors are suited as well. The tube assembly should comprise appropriate connection means for connecting the filter-containing compartment and the expansion chamber, such as, e.g., dry-to-dry aseptic connections, e.g., READYMATE® connections from GE Healthcare. This does not preclude the use of other appropriate connections.

Suitable materials for the filter-containing compartment (6) nonexclusively include plastics like polysulfone, metal or glass. In preferred embodiments, materials appropriate for gamma sterilization and preferably commonly used as disposable materials (i.e., generally for one-time use) are suitable materials. The skilled man in the art knows what materials are commonly used and suitable for this application. Most preferably, the filter-containing compartment is made out of disposable material, and preferred examples include polysulfone. The filter-containing compartment (6) comprises a filter (8). Suitable filter elements nonexclusively include hollow fiber filters, screen filters, and the like. Most preferably, the filter element is a hollow fiber filter or filters consisting of a screen mesh. Suitable hollow fiber filtration membranes or screen filters are commonly available from various vendors, e.g., ready-to-process hollow fibers from GE Healthcare or WaterSep, Krosflo hollow fibers from Spectrum, and Microza hollow fibers from Pall. In certain preferred embodiments, the filter is positioned longitudinally from the entrance end (7) to the exit end (9) of the filter-containing compartment (6), which enables tangential flow of the fluid along the filter. When the filter is a hollow fiber filter, the axes of the hollow fibers preferably extend longitudinally from the entrance end (7) to the exit end (9) of the filter-containing compartment (6).

The expansion chamber (17) is connected to the exit end (9) of the filter-containing compartment (6) on one side and to a gas flow controller (28) on the other side. The expansion chamber (17) is capable of aspirating and receiving the fluid from the vessel (1) through filter (8) into the expansion chamber (17) and alternately expelling the fluid from the expansion chamber (17) back into the vessel (1) through the filter (8). In this way, an alternating tangential flow of fluid is generated through filter (8). The tangential flow can be harvested through a fluid harvest port (10) into a permeate line (11). In a preferred embodiment, the permeate line (11) comprises a permeate pump (12), which regulates the tangential flow.

Filter (8) can be a hollow fiber filter, a mesh filter or the like. In the case where filter (8) is a hollow fiber filter, both ends, the entrance end and the exit end of filter (8) are sealed against the housing wall of the filter-containing compartment (6) to prevent mixing of the retentate side, and the permeate (filtered) side of the filter. The retentate side of the fiber is the lumen side of the hollow fiber and the permeate (or filtrate) side is the shell side of the hollow fiber. Such a leak proof seal can be formed by a number of methods known in the art, including O-rings, gaskets or any other means that form an impenetrable barrier between the circumference at each end of the filter and the inner wall of the housing. Alternating flow of retentate between the expansion chamber (17) and vessel (1) is through the lumen side of the filter (8) in the filter-containing compartment (6).

The expansion chamber (17) has an entrance end, also named first opening (16), through which fluid flows from the exit end (9) of the filter-containing compartment (6). The exit end of the expansion chamber, also named second opening (24), is operably connected to a gas flow controller (28) by a gas line (22). In a preferred embodiment, the gas line (22) is a reversible inlet/exhaust line. In other embodiments, separate inlet and exhaust gas lines are provided (not shown). The fluid contained in the fluid storage vessel (1) and the filter-containing compartment (6) is alternately drawn into the expansion chamber (17) and expelled from it. The back and forth movement of the fluid is actuated by alternately applying sufficient positive and negative pressure into the expansion chamber. The positive pressure, which is defined as higher pressure than the pressure in the filter-containing compartment (6), is preferably obtained by feeding a gas, such as compressed air, through the gas line (22). Negative pressure, which is defined as a lower pressure than the pressure in the filter-containing compartment (6), is preferably obtained by applying under-pressure or vacuum into the expansion chamber. The positive and negative pressure can be applied using means and methods that are well known to the skilled person, and such means and methods need not be further elaborated here.

The expansion chamber (17) can be any type of container having any type of shape such as, e.g., a cylindrical, square, or circular shape (not limiting). In certain embodiments, the chamber has a cylindrical shape. The expansion chamber according to the disclosure contains no separation means, such as a diaphragm or any other moving parts or physical barriers, between the first and second openings. The expansion chamber comprises one room only and is not separated into two or more compartments. In operations, the expansion chamber comprises a direct gas-liquid interface, without separation means, that is formed by the liquid contained in the system, which is in direct contact with the gas phase provided by the gas flow controller.

The chamber must be suited for containing both the liquid provided from the vessel and the gas provided from the gas flow controller through the gas line (22). Suitable materials for the expansion chamber nonexclusively include plastics like polysulphon. Alternatively, the chamber is made of metal such as stainless steel. In preferred embodiments, materials that are appropriate for gamma sterilization are used as suitable materials. In further preferred embodiments, materials that are commonly used as single-use materials are used as suitable materials. In further preferred embodiments, materials that are appropriate for gamma sterilization and that are commonly used as single-use materials, are used as suitable materials. The skilled man in the art would know what materials are commonly used and suitable for this application. Single-use materials are as the name states generally appropriate for a one-time use. Usually, they are sterilized once, used subsequently and disposed. As opposed to traditional materials such as, e.g., stainless steel, they do not require being repeatedly washed, assembled and sterilized. The use of components made from single-use materials, also called disposables, in the pharmaceutical industry, offers the advantage of not having to perform the very costly validation of the cleaning, assembly and sterilization processes of the components. Disposable systems are generally less expensive and a spent system can be replaced easily by an unused system, even during the process.

The expansion chamber (17) is preferably made, at least in part (e.g., comprising a "window") or substantially completely, from a transparent material in order to visualize the liquid level in the chamber. The liquid that is drawn into the chamber preferably should not exceed a certain maximum level within the container. The maximum liquid level is measured with a level sensor (24), as indicated in FIG. 1, mounted on the surface of the container. The level sensor (24) is named "Level sensor high high" (LSHH). In the preferred embodiment as indicated in FIG. 1, the container optionally indicates two levels on its surface: level sensor low (LSL) and level sensor high (LSH), which are measured by a level sensor low (25) and a level sensor high (26). In preferred embodiments, during the filtration process, the liquid level should normally fluctuate approximately between the LSL and LSH. When expelled from the expansion chamber (17), the liquid should preferably not drop below approximately the LSL level. When aspirated from the fluid storage vessel (1) into the expansion chamber (17), the liquid should preferably not go higher than approximately the LSH level.

The expansion chamber (17) may be further provided with two level sensors, preferably mounted on the expansion chamber's surface, which determine the fluid level in the expansion chamber (17) and provide feedback to the gas flow controller (28), which, in turn, actuates the alternating positive and negative pressure cycle in the expansion chamber. Level sensors may alternatively be inside the expansion chamber (17), but it is preferred to mount them on its surface (i.e., on the exterior side of the expansion chamber), since contact with the filtered fluid (which is inside and may contact an interior side of the expansion chamber) is then avoided. Level sensors as such are known in the art and can use a variety of parameters to measure the level of fluid in the expansion chamber, e.g., the K1R87xXT2 from Wenglor, which is based on light scattering, or the sensor from Aquasant Messtechnik based on capacity measurements. In a preferred embodiment, microwave emitters, e.g., Vegamip from Vega, are used for level detection. The sensors are particularly accurate in the presence of foam on the medium surface.

The exit end (18) of the expansion chamber (17) is connected to a gas line (22), which, in turn, is connected to a gas flow controller (28). Preferably, the gas line (22) comprises a sterile filter (21) in order to provide for sterile gas, e.g., compressed air, into the expansion chamber. Herewith, the risk of contaminating the liquid phase in the expansion chamber is minimized. In a preferred embodiment, the sterile filter (21) is an air filter, which preferably is provided with a heater in order to prevent blockage of the filter due to wetting by vapor generated in the expansion chamber. When the gas line (22) comprises a sterile filter (21), as depicted in FIG. 1, the filter is further connected to the expansion chamber (17) by means of an additional gas line (20).

The gas flow controller (28) provides for positive and negative pressure through the gas line (22), which preferably is a reversible inlet/exhaust line. The positive pressure can, for instance, be generated directly, for example, via a compressed air supply. The negative pressure is generated in the controller, for instance, by creating a vacuum. The vacuum can be generated by a vacuum pump or, for example, a vacuum injector. A vacuum injector is a pump-like device that uses the Venturi effect of a converging-diverging nozzle to convert the pressure energy of a motive fluid to velocity energy, which creates a low-pressure zone that draws in and entrains a suction fluid. After passing through the throat of the injector, the mixed fluid expands and the velocity is reduced, which results in recompressing the mixed fluids by converting velocity energy back into pressure energy. The motive fluid may be a liquid, steam or any other gas. The entrained suction fluid may be a gas, a liquid, a slurry, or a dust-laden gas stream. In a preferred embodiment, the gas flow controller does not require a separate vacuum supply. Alternatively to a vacuum injector, other known means and methods for creating underpressure in the expansion chamber (17) may be used. Instead of compressed air, other gases or gas mixtures may be used, e.g., nitrogen, nitrogen/oxygen or nitrogen/oxygen/carbon dioxide mixtures, etc.

During the filtration process, the liquid contained in the fluid storage vessel (1) is aspirated out of the vessel (1), through the filter (8), into the expansion chamber (17) and alternately expelled from it back into the vessel (1). When the liquid is aspirated out of the vessel (1), negative pressure is applied until the level sensor LSH (26) is responding, that is, until the liquid is drawn into the expansion chamber (17) and the level in the chamber (17) reaches an upper limit (LSH). This triggers a switch to apply positive pressure. The positive pressure is then applied until the level detector LSL (25) is responding, that is, until the liquid is expelled from the expansion chamber (17) and the liquid level in the chamber (17) reaches a lower limit (LSL). This triggers the switch again to apply negative pressure. As a result, the fluid in the system flows back and forth through the filter (8) in a controlled way, providing for a tangential fluid flow into the permeate line (11).

Gas flow controllers as such are known and can be used according to methods known by the skilled person, in accordance herewith. The gas flow controller (28) provides for positive and negative pressure into the expansion chamber (17). In certain embodiments, the gas flow controller (28) may comprise a pressure-measuring device (32), such as a pressure sensor, which serves to monitor and/or regulate the pressure in the gas line (22). In addition, the gas flow controller may comprise a pressure-measuring device (30), which serves to measure the pressure in the permeate line (11). In certain embodiments, the gas flow controller (28) is connected to an air or other gas supply, which provides the gas flow controller with air or gas, from which the pressure can optionally be reduced with a pressure reducer (46). The gas that may be reduced in flow is further directed either through a pressure controller (44) and control valve (40) toward the gas line (22) in order to provide for the positive pressure or, alternatively, through a pressure controller (42) and vacuum injector (36) in order to provide for negative pressure into the gas line (22) and the expansion chamber (17). In addition, the gas flow controller may comprise a shut-off valve (38), which is functionally in contact with the level sensors (25, 26) and which closes when the fluid in the expansion chamber (17) has reached the maximal level (LSH). The gas flow controller (28) further comprises a switch-over valve (34), which is in contact with the level sensors (25, 26) and which determines whether compressed air (having higher pressure than the pressure in the filter-containing compartment) or vacuum or under-pressure (as compared to the pressure in the filter-containing compartment) is applied into the gas line (22).

In one embodiment, the liquid level in the expansion chamber is controlled by level sensors, such as light switches or microwave emitters. Several of the level sensors are positioned along the expansion chamber and allow calculating the speed of the medium front in the expansion chamber. The speed of the medium can be determined by continuously measuring the time ($\Delta t$) spent by the medium between the LSL level and LSH level. Variations in speed can indicate that the hollow fiber membrane is about to clog or that it has clogged. By measuring the speed, it is possible to automatically control the positive and negative pressure cycle and therewith adjust the medium flow rate or adjust the medium aspiration/expulsion cycle, in order to unclog the hollow fiber that shows signs of clogging.

In another embodiment, the positive and negative pressure cycle in the expansion chamber can be regulated based on particle size distribution and load of the cell suspension. Particle size distribution and load can be measured with a particle sizer, e.g., a CASY® counter. The particle size distribution and load output values can be directed to the gas flow controller in order to regulate the positive and negative pressure cycle. This embodiment allows the possibility to prepare a calibration curve correlating the hollow fiber performance to the cell density and allowing automatic flow control according to the cell density input.

This has a significant advantage over the filtration systems currently used in which action can only be taken manually by an operator once the hollow fiber shows signs of clogging. Hence, the system works automatically and proactively.

All these control features are not available in the currently existing filtration systems (such as the ATF system currently commercially available and disclosed in U.S. Pat. No. 6,544,424). The cycle number is the only parameter that is controlled in these systems. The cycle time is adapted manually by an operator based on gut-feeling.

The filter-containing compartment (6) is further provided with a permeate port (10), which allows the tangential fluid flow to be recovered. The permeate exits the filter-containing compartment through the permeate port (10) into a permeate line (11). In the most preferred embodiment, a permeate pump (12) is connected to the permeate line (11). The permeate pump (12) is suitable as a means for controlling the removal of filtered fluid (permeate) from the system and to serve as a check valve to regulate the unrestricted flow of permeate from the filter-containing compartment (6). Pressure in the permeate line may be monitored by a pressure sensor (30), as shown in FIG. 1.

While a single embodiment hereof has been disclosed in detail, many other variations are contemplated. For instance, in another embodiment of the invention, a screen mesh filter module could be used instead of the hollow fiber filter module described above. A screen mesh that is appropriate in the disclosure was described in, e.g., U.S. Pat. No. 6,544,424.

In some applications, it may be desirable to penetrate the process vessel (1) through an opening other than the bottom side opening described above. Not shown is a top penetrating port through a head plate of the process vessel (1). In this case, the relationship between system components including the fluid transfer line (4), the filter-containing compartment (6), the expansion chamber (17) and the gas flow controller (28) remains the same. Note, however, that to generate alternating tangential flow, a dip tube (not shown) would then be used to connect the filtration system to the liquid in the process vessel (1). Filtered harvest (permeate) would similarly be collected from the filter-containing compartment (6), through a permeate port (10) into the permeate line (11). The liquid volume that is removed from the system (through the permeate line) may be restored into the system by a level control mechanism that activates an additional pump in order to pump liquid into the vessel.

Other variations of the invention are also possible. For example, multiple filter-containing compartments may be connected in parallel to a single vessel. Each filter-containing compartment may be connected to a separate expansion chamber. When multiple filter-containing compartments are disposed in parallel formation and a first filter is blocked, the process can continue with a second or third filter-containing compartment. Herewith the continuity of the process is guaranteed.

Figure 2:
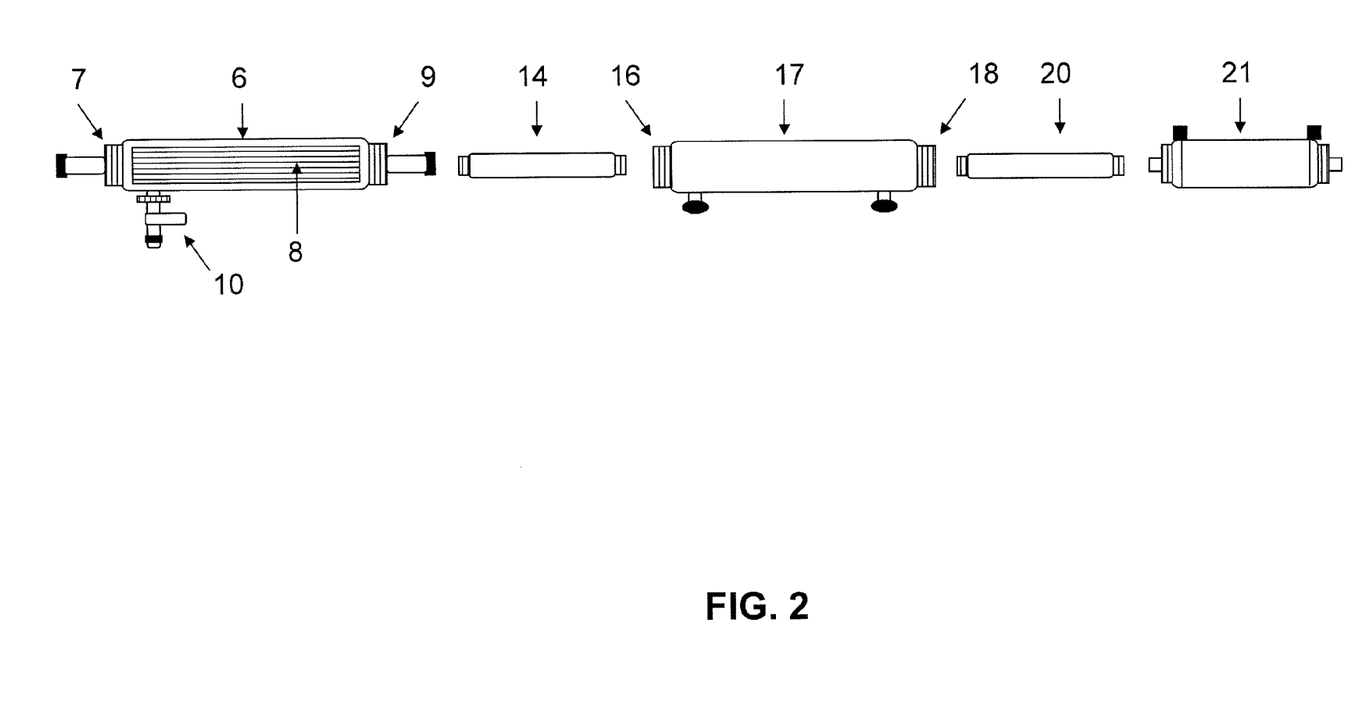
FIG. 2 shows an assembly comprising an expansion chamber, a filter-containing compartment and an air filter.

One further aspect of the disclosure relates to an assembly as depicted in FIG. 2, comprising an expansion chamber (17)

assembled to a filter-containing compartment (6) on one side and to an air filter (21) on the other side, wherein the assembled components are preferably made of disposable materials, and preferably are sterile (at least on the inside that is intended to be in contact with the fluid that is to be filtered). Single-use materials (or disposables) are defined previously and the skilled person would know which materials are appropriate for this purpose.

The expansion chamber (17) of the assembly has an entrance end, also named first opening (16), which is coupled to the exit end or retentate end (9) of the filter-containing compartment (6). Both components are connected directly to each other or via an intermediate tube assembly (14), as shown in FIG. 2. When directly connected to each other, an appropriate connection is, e.g., a dry-to-dry aseptic connection, as, e.g., a READYMATE® connection from GE Healthcare or a Kleenpack connection from Pall. When an intermediate tube assembly is used, the tube assembly preferably comprises a tubing of silicone, bioprene, C-flex or the like. Each tube end comprises a connecting means in order to appropriately connect the intermediate tube assembly (14) to the filter-containing compartment (6) and the expansion chamber (17). Suited connections can, for instance, be dry-to-dry aseptic connections, such as, e.g., READYMATE® connections or the like.

The exit end, also named second opening (18) of the expansion chamber, is connected to an air filter (21). Both components are connected directly to each other or via an intermediate tube assembly (20), as shown in FIG. 2. Appropriate connections are similar to those connecting the expansion chamber to the filter-containing compartment.

In one embodiment of the disclosure, the expansion chamber of the assembly contains no separation means, such as a diaphragm or any other moving parts or physical barriers, between the first and second opening. The expansion chamber comprises one room only and is not separated into two or more compartments. Herewith, the expansion chamber, when built in the assembly and when connected to a gas flow meter and a fluid storage vessel according to the invention, comprises a direct gas-liquid interface without separation means that is formed by the liquid contained in the system, which is in direct contact with the gas phase provided by the gas flow controller.

In one embodiment, the assembly will be sterilized, preferably by gamma irradiation, and packaged for storage. The pre-sterilized assembly can be sterilely connected to a fluid vessel and a gas flow controller in order to perform tangential filtration according to the invention. The advantage of the assembly is that it contains no moving parts and is, therefore, not prone to wastage or breakage of the system during the filtration process. In a second place, the assembly, which is pre-sterilized, allows the filtration process to start right after it has been connected. No costly cleaning and sterilization validation procedures are required.

Another aspect hereof relates to a method for preparing an assembly as previously described comprising the steps of assembling a filter-containing compartment on to a first opening of an expansion chamber and assembling an air filter on to a second opening of the expansion chamber.

Another aspect hereof relates to a kit of parts comprising a filter-containing compartment, an expansion chamber and a sterile air filter, which can be used for providing an assembly as described herein (FIG. 2). The components of the kit of parts are preferably disposables. The kit of parts provides for a very robust and cost-effective assembly to be used in a system for tangential flow filtration according to the invention.

The system hereof may be used for filtering, concentrating, clarifying or otherwise conditioning a fluid or process medium when used with the appropriate filter element. The system may also be used as a sampler, suitable for extracting filtered stream from a process vessel while allowing continuous monitoring and analysis of the process. The back and forth flow of medium between vessel and filter allows continuous equilibration of the process medium between these two compartments. In certain embodiments, the filtered stream may, therefore, be considered representative of the content in the vessel.

The system hereof is most preferably used for filtering fluids, such as biological fluids. Nonexclusive examples of biological fluids include suspension cultures, microcarrier-based cultures, blood, and other fluids containing animal, microbial or plant cells. Although a preferred embodiment of the disclosure is disclosed with regard to filtering a biological fluid, it is understood that the disclosure can be used for filtering other liquids.

In a preferred embodiment, the system hereof can be used for the production of biologicals such as recombinant proteins as described in, e.g., WO 2008/006494, or such as viruses as described in WO 2010/060719. The filtration system used in these references could be replaced by the PACS system.

Example 1

Use of PACS System for Culturing Cells in Perfusion

Figure 3:
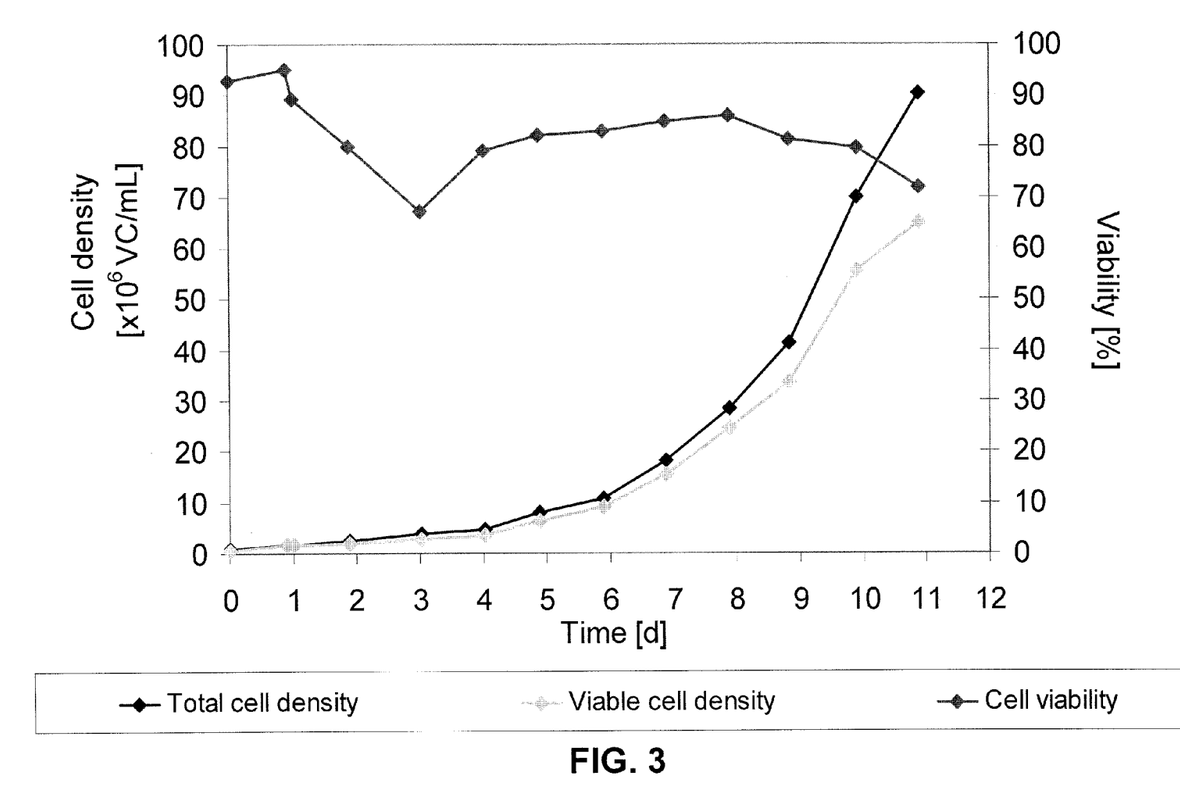
FIG. 3 shows a cell growth curve in a 10 L bioreactor coupled to a PACS system.

PER.C6® cells were precultured in PERMEXCIS® medium in a CULTIBAG® rocking motion system. Subsequently, the cells were transferred for inoculation into a stirred 10 L bioreactor, which was connected to a PACS system according to the disclosure. Permeate withdrawal using the PACS system was started when a cell density of approximately $2 \times 10^6$ viable cells/mL was reached (two days post inoculation). After nine days of perfusion, the cell culture reached a cell density of more than $60 \times 10^6$ viable cells/mL, as shown in FIG. 3. This experiment shows that the PACS system can be successfully used for growing cells in perfusion.

Example 2

Figure 4:
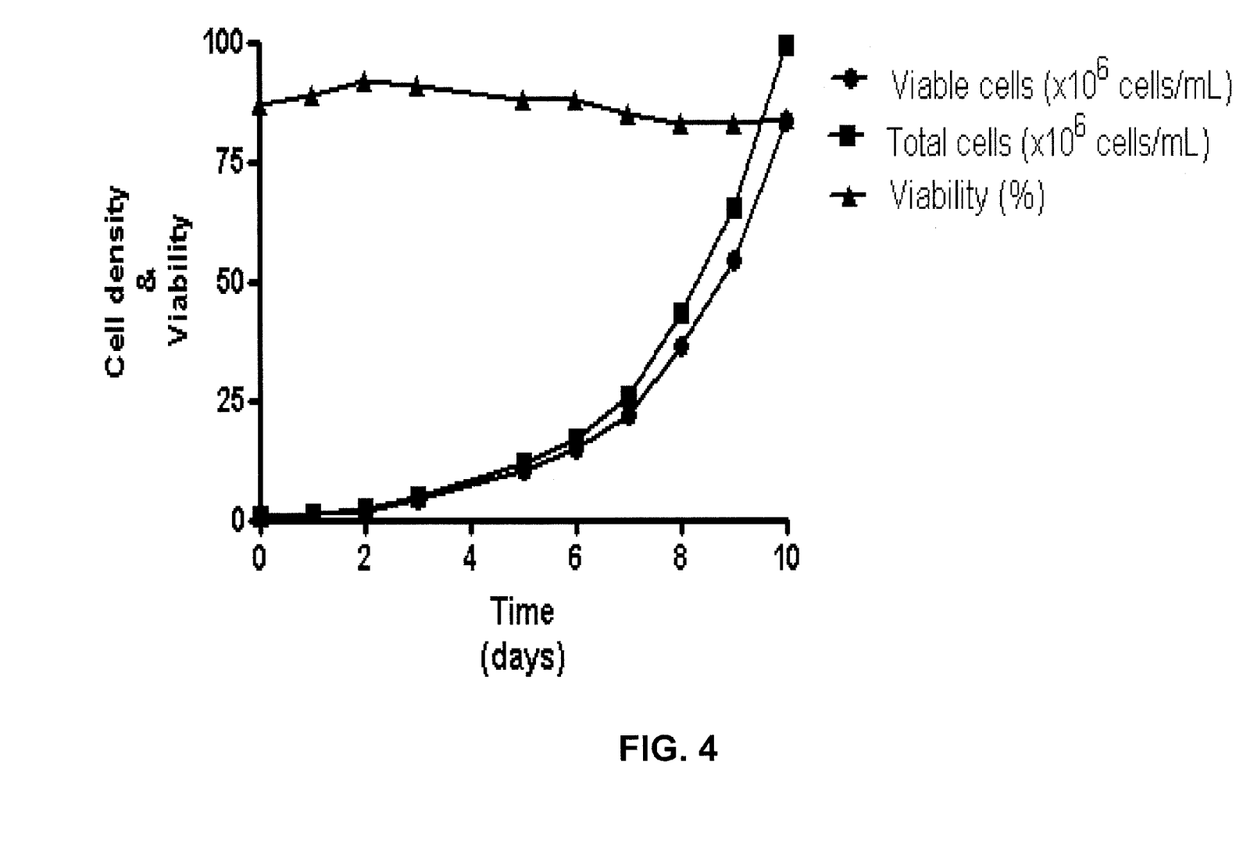
FIG. 4 shows a cell growth curve in a 10 L bioreactor coupled to a PACS system.

Use of PACS System for Culturing Cells at High Cell Densities and Propagating Adenovirus PER.C6® cells were thawed and propagated in serum-free culture medium in a 20 L WAVE® bioreactor at a working volume of 10 L. The cells were propagated at 37° C. with a $CO_2$ and air overlay of 0.18 L/minute and 20 mL/minute, respectively. Cell counts were performed on a daily basis. On day 4 after inoculation of the WAVE® bioreactor, a back dilution was performed. Day 7 post inoculation, the cell suspension was used to inoculate a 10 L stirred bioreactor, coupled to a PACS system, at a cell density of $0.57 \times 10^6$ total cells/mL. Cells were propagated in the 10 L bioreactor at 37° C., DO of 40%, and a pH of 7.3. The PACS system was started directly after inoculation of the bioreactor, perfusion was started 2 days post inoculation at a cell density of approximately $2 \times 10^6$ viable cells/mL. After 8 days of perfusion, a cell density of $83.2 \times 10^6$ viable cells/mL was reached. The cell growth is presented in FIG. 4.

On day 10 post inoculation, the suspension contained in the 10 L bioreactor was transferred to a 50 L disposable bioreactor containing 40 L fresh medium. This resulted in a cell density of $20.94 \times 10^6$ total cells/mL (90% viability, hence $18.86 \times 10^6$ viable cells/mL) at inoculation.

Subsequently, the 50 L bioreactor, which was connected to a PACS system, was infected with an Ad35 adenovirus at an MOI of 70 virus particles/cell (VP/cell) and incubated at 36° C., pH 7.3 and DO of 40%. The PACS system was started 5 hours post infection at a medium refreshment rate of 2 vessel volumes per day for the subsequent 40 hours. On day 3 post infection, the 50 L bioreactor was sampled for measuring virus production by AEX-HPLC. To release the virus from the cells, 1 mL sample was mixed with 100 μL 10% TRITON® X-100 and incubated at 37° C. for 30 minutes. After incubation, the sample was mixed with 2.42 μL benzonase/MgCl$_2$ followed by a subsequent incubation step of 30 minutes at 37° C. Finally, 100 μL 50% sucrose was added to the samples. After a centrifugation step of 5 minutes at 2500 g, the samples were stored at a temperature below −65° C. until analysis by AEX-HPLC.

The AEX-HPLC results showed that a yield of $2.08 \times 10^{12}$ VP/mL was reached on day 3 post infection.

These results demonstrate that the PACS system can be used for culturing cells at very high cell densities, up to more than $80 \times 10^6$ viable cells/mL. Furthermore, these results show that the PACS system can be used for propagating virus on high cell density cultures and increasing the volumetric yields almost ten times compared to a batch process.

The invention claimed is:

1. A fluid filtration system comprising:
a) a liquid containing bioreactor;
b) a filter-containing compartment;
c) a liquid transfer line connecting the storage vessel to an entrance end of a filter-containing compartment, which liquid transfer line is capable of directing the liquid from the bioreactor into the entrance end of the filer-containing compartment;
d) a expansion chamber with at least two openings, wherein a first opening is connected at an exit end of the filter-containing compartment and wherein a second opening is connected to a gas flow controller, wherein the expansion chamber contains no separation means between the first and second openings, and wherein at least one level sensor is mounted on or in the expansion chamber to indicate the level of fluid in the expansion chamber;
e) a gas flow controller in communication with the level sensor for alternatively providing the expansion chamber with positive qas pressure and negative pressure; and
f) a liquid harvest port connected to the filter-containing compartment for removing filtered liquid from the filter-containing compartment.

2. A fluid filtration system according to claim 1, wherein the expansion chamber is connected to the gas flow controller with a gas line.

3. The fluid filtration system of claim 1, wherein the gas line comprises a filter between the expansion chamber and the gas flow controller.

4. The fluid filtration system of claim 1, wherein the filter-containing compartment contains a hollow fiber filter.

5. The fluid filtration system of claim 1, wherein at least two level sensors are mounted on or in the expansion chamber.

6. A fluid filtration system according to claim 5, wherein said level sensors are capable of measuring a minimal and a maximal fluid level in the expansion chamber, and functionally coupled to the gas flow controller.

7. The fluid filtration system of claim 1, capable of alternately aspirating the fluid of the system from the bioreactor, through the filter-containing compartment into the expansion chamber, and expelling the fluid from said expansion chamber through the filter-containing compartment back into the bioreactor, wherein fluid aspiration is performed by applying negative pressure into the expansion chamber and fluid expulsion is performed by applying positive pressure into the expansion chamber.

8. The fluid filtration system of claim 1, wherein said negative pressure is obtained by creating a vacuum in the expansion chamber and positive pressure is obtained by injecting gas.

9. The fluid filtration system of claim 1, wherein the filter in the filter-containing compartment comprises a plurality of bundled hollow fibers whose axes extend longitudinally from the entrance end to the exit end of the filter-containing compartment.

10. The fluid filtration system of claim 9, wherein the filter-containing compartment and the expansion chamber are disposable.

11. A process for filtering a fluid, the process comprising the steps of:
a) providing a fluid filtration system comprising:
a liquid containing bioreactor;
a filter-containing compartment;
a liquid transfer line connecting the bioreactor to an entrance end of the filter-containing compartment, which transfer line is capable of directing a fluid from the bioreactor into the entrance end of the filter-containing compartment;
a expansion chamber connected on one side to an exit end of the filter-containing compartment allowing for liquid from said compartment to enter the chamber and on the other side to a gas flow controller, which alternatively provides negative and positive pressure into the expansion chamber thereby aspirating the liquid from the exit end of the filter-containing compartment and expelling liquid back into the exit end of the filter-containing compartment, forming a direct gas-liquid interface without separation means into the expansion chamber;
and a permeate port connected to the filter-containing compartment for removing filtered fluid from the filter-containing compartment;
wherein the gas flow controller is in communication with at least one level sensor mounted on or in the expansion chamber to indicate the level of fluid in the expansion chamber;
b) drawing liquid out of the bioreactor through the filter into the expansion chamber by applying negative pressure into the expansion chamber;
c) expelling the liquid from the expansion chamber through the filter back into the bioreactor by applying a positive pressure into the expansion chamber;
and
d) removing the filtered liquid from the filtration system.

12. The process of claim 11, wherein the filter-containing compartment and/or the expansion chamber are disposable.

13. The process of claim 12, wherein the positive pressure and negative pressure are regulated by said one or more level sensors which measure the fluid level in the expansion chamber and control the positive and negative pressures applied thereto.

14. The process of claim 11, wherein the filter-containing compartment contains a hollow fiber filter.

15. The process of claim 11, wherein the negative pressure is obtained by creating a vacuum in the expansion chamber and the positive pressure is obtained by injecting gas into the expansion chamber.

16. The fluid filtration system of claim 3, wherein the filter is a sterile filter.

17. The process of claim 12, wherein the filter-containing compartment, the expansion chamber, the bioreactor and the fluid transfer line are disposable.

* * * * *

UNITED STATES PATENT AND TRADEMARK OFFICE
CERTIFICATE OF CORRECTION

PATENT NO. : 8,845,902 B2  
APPLICATION NO. : 13/983982  
DATED : September 30, 2014  
INVENTOR(S) : Alain Pralong and Hans Ulrich Dellenbach

Page 1 of 1

It is certified that error appears in the above-identified patent and that said Letters Patent is hereby corrected as shown below:

In the claims:

| | | |
|---|---|---|
| CLAIM 1, | COLUMN 15, LINE 38, | change "a expansion" to --an expansion-- |
| CLAIM 1, | COLUMN 15, LINE 49, | change "qas" to --gas-- |
| CLAIM 11, | COLUMN 16, LINE 34, | change "a expansion" to --an expansion-- |

Signed and Sealed this  
Twenty-ninth Day of December, 2015

Michelle K. Lee  
*Director of the United States Patent and Trademark Office*